US009557330B2

(12) United States Patent
Siciliano et al.

(10) Patent No.: US 9,557,330 B2
(45) Date of Patent: *Jan. 31, 2017

(54) DEVICE FOR DETECTION OF ANALYTES AND USES THEREOF

(75) Inventors: Nicholas A. Siciliano, Cherry Hill, NJ (US); Martin Joseph Bouliane, Carlsbad, CA (US)

(73) Assignee: Invisible Sentinel, Inc., Philadelphia, PA (US)

( * ) Notice: Subject to any disclaimer, the term of this patent is extended or adjusted under 35 U.S.C. 154(b) by 1184 days.

This patent is subject to a terminal disclaimer.

(21) Appl. No.: 13/500,997

(22) PCT Filed: Oct. 12, 2010

(86) PCT No.: PCT/US2010/052287
§ 371 (c)(1),
(2), (4) Date: Jun. 26, 2012

(87) PCT Pub. No.: WO2011/044574
PCT Pub. Date: Apr. 14, 2011

(65) Prior Publication Data
US 2012/0270229 A1    Oct. 25, 2012

Related U.S. Application Data

(60) Provisional application No. 61/250,286, filed on Oct. 9, 2009.

(51) Int. Cl.
*G01N 33/558* (2006.01)
*G01N 33/543* (2006.01)
*C12Q 1/04* (2006.01)
*G01N 33/53* (2006.01)

(52) U.S. Cl.
CPC .......... *G01N 33/54386* (2013.01); *C12Q 1/04* (2013.01); *G01N 33/5302* (2013.01); *G01N 2333/205* (2013.01); *G01N 2333/245* (2013.01); *G01N 2333/255* (2013.01)

(58) Field of Classification Search
None
See application file for complete search history.

(56) References Cited

U.S. PATENT DOCUMENTS

| 3,581,227 A | 5/1971 | Podgorski |
| 4,246,339 A | 1/1981 | Cole et al. |
| 4,254,084 A | 3/1981 | Blum |
| 4,444,879 A | 4/1984 | Foster et al. |
| 4,446,232 A | 5/1984 | Liotta |

(Continued)

FOREIGN PATENT DOCUMENTS

| AU | 200025390 B2 | 7/2000 |
| CA | 2024458 A1 | 3/1991 |

(Continued)

OTHER PUBLICATIONS

Final Office Action dated Mar. 17, 2015 from related U.S. Appl. No. 13/789,002.

(Continued)

*Primary Examiner* — Chris L Chin
(74) *Attorney, Agent, or Firm* — Pepper Hamilton LLP

(57) ABSTRACT

Devices and methods for the detection of antigens are disclosed. Devices and methods for detecting food-borne pathogens are disclosed.

26 Claims, 9 Drawing Sheets

(56) References Cited

U.S. PATENT DOCUMENTS

| | | | |
|---|---|---|---|
| 4,727,019 A | 2/1988 | Valkirs et al. |
| 4,797,260 A | 1/1989 | Parker |
| 4,828,801 A | 5/1989 | Lombardy wife Alric et al. |
| 4,920,046 A | 4/1990 | McFarland et al. |
| 4,994,240 A | 2/1991 | Hayashi |
| 5,003,988 A | 4/1991 | Guirguis |
| 5,133,363 A | 7/1992 | Guirguis |
| 5,137,691 A | 8/1992 | Parker |
| 5,141,850 A | 8/1992 | Cole et al. |
| 5,149,622 A | 9/1992 | Brown et al. |
| 5,155,022 A | 10/1992 | Naqui et al. |
| 5,155,049 A | 10/1992 | Kauvar et al. |
| 5,160,701 A | 11/1992 | Brown, III et al. |
| 5,166,054 A | 11/1992 | Naqui |
| 5,167,924 A | 12/1992 | Clark |
| 5,175,270 A | 12/1992 | Nilsen et al. |
| 5,185,127 A | 2/1993 | Vonk |
| 5,215,102 A | 6/1993 | Guirguis |
| 5,252,496 A | 10/1993 | Kang et al. |
| 5,358,690 A | 10/1994 | Guirguis |
| 5,451,504 A | 9/1995 | Fitzpatrick et al. |
| 5,474,902 A | 12/1995 | Uylen et al. |
| 5,541,069 A | 7/1996 | Mortensen et al. |
| 5,559,041 A | 9/1996 | Kang et al. |
| 5,620,657 A | 4/1997 | Sizto et al. |
| 5,741,662 A | 4/1998 | Madsen |
| 5,922,615 A | 7/1999 | Nowakowski et al. |
| 5,948,695 A * | 9/1999 | Douglas ............ B01L 3/5023 422/401 |
| 5,962,250 A | 10/1999 | Gavin et al. |
| 6,555,390 B2 | 4/2003 | Chandler |
| 6,716,641 B1 | 4/2004 | Sundrehagen |
| 6,766,817 B2 | 7/2004 | Da Silva |
| 6,770,447 B2 | 8/2004 | Maynard et al. |
| 7,052,831 B2 | 5/2006 | Fletcher et al. |
| 7,205,159 B2 | 4/2007 | Cole |
| RE39,664 E | 5/2007 | Gordon et al. |
| 7,285,255 B2 | 10/2007 | Kadlec et al. |
| 7,300,750 B2 | 11/2007 | Smart et al. |
| 7,377,904 B2 | 5/2008 | Conway et al. |
| 7,393,697 B2 | 7/2008 | Charlton |
| 7,435,577 B2 | 10/2008 | Lawrence |
| 7,488,606 B2 | 2/2009 | Fleming et al. |
| 7,497,997 B2 | 3/2009 | Glezer et al. |
| 7,531,362 B2 | 5/2009 | Chan |
| 7,582,258 B2 | 9/2009 | Ruhl et al. |
| 7,638,093 B2 | 12/2009 | Wang et al. |
| 7,803,319 B2 | 9/2010 | Yang et al. |
| 7,815,854 B2 | 10/2010 | Cohen |
| 7,819,822 B2 | 10/2010 | Calasso et al. |
| 8,012,770 B2 * | 9/2011 | Siciliano ............ B01L 3/5023 422/401 |
| 8,183,059 B2 * | 5/2012 | Siciliano ............ B01L 3/5023 422/401 |
| 8,476,082 B2 * | 7/2013 | Siciliano ............ B01L 3/5023 422/401 |
| 2002/0115198 A1 | 8/2002 | Nerenberg et al. |
| 2002/0146346 A1 | 10/2002 | Konecke |
| 2002/0172937 A1 | 11/2002 | Dave et al. |
| 2002/0187561 A1 | 12/2002 | Wong et al. |
| 2003/0021727 A1 | 1/2003 | Weyker et al. |
| 2003/0073248 A1 | 4/2003 | Roth et al. |
| 2003/0207442 A1 | 11/2003 | Markovsky et al. |
| 2003/0207466 A1 | 11/2003 | Po Lee |
| 2004/0002063 A1 | 1/2004 | Chan et al. |
| 2004/0018576 A1 | 1/2004 | DeMatteo et al. |
| 2004/0214253 A1 | 10/2004 | Paek |
| 2004/0256230 A1 | 12/2004 | Yager et al. |
| 2005/0069962 A1 | 3/2005 | Archer et al. |
| 2005/0124077 A1 | 6/2005 | Cole |
| 2005/0130294 A1 | 6/2005 | Randall et al. |
| 2005/0163658 A1 | 7/2005 | Wang et al. |
| 2005/0191620 A1 | 9/2005 | McDevitt et al. |
| 2005/0277202 A1 | 12/2005 | Fleming et al. |
| 2006/0275851 A1 | 12/2006 | Emmert-Buck et al. |
| 2007/0004003 A1 | 1/2007 | Kitamoto et al. |
| 2007/0009911 A1 | 1/2007 | Joo et al. |
| 2007/0020768 A1 | 1/2007 | Rundstrom et al. |
| 2007/0098601 A1 | 5/2007 | Mabuchi et al. |
| 2007/0190667 A1 | 8/2007 | Cole |
| 2007/0202542 A1 | 8/2007 | Babu et al. |
| 2007/0218500 A1 | 9/2007 | Mikoshiba et al. |
| 2007/0224701 A1 | 9/2007 | Rosenstein |
| 2008/0013949 A1 | 1/2008 | Yoshikane et al. |
| 2008/0019866 A1 | 1/2008 | Paek et al. |
| 2008/0199851 A1 | 8/2008 | Egan et al. |
| 2008/0318342 A1 | 12/2008 | Durack |
| 2009/0108013 A1 | 4/2009 | Van Der Velde et al. |
| 2009/0140471 A1 | 6/2009 | Fletcher et al. |
| 2009/0148933 A1 | 6/2009 | Battrell et al. |
| 2009/0272974 A1 | 11/2009 | Park et al. |
| 2009/0311668 A1 | 12/2009 | Cheng |
| 2010/0009387 A1 | 1/2010 | Cheng |
| 2010/0034699 A1 | 2/2010 | Chan |
| 2010/0233028 A1 | 9/2010 | Iwasaki et al. |
| 2010/0261206 A1 | 10/2010 | Choi et al. |
| 2010/0322823 A1 | 12/2010 | Surapaneni et al. |
| 2010/0323369 A1 | 12/2010 | Marlborough et al. |
| 2011/0027908 A1 | 2/2011 | Siciliano et al. |
| 2011/0117673 A1 | 5/2011 | Johnson et al. |

FOREIGN PATENT DOCUMENTS

| | | |
|---|---|---|
| CA | 2037521 A1 | 11/1991 |
| CA | 2060216 A1 | 9/1992 |
| CN | 1979164 A | 6/2007 |
| CN | 1989413 | 6/2007 |
| CN | 101339190 A | 1/2009 |
| CN | 101655494 A | 2/2010 |
| CN | 101726594 A | 6/2010 |
| EP | 0067921 A1 | 12/1982 |
| EP | 0246900 A1 | 11/1987 |
| EP | 0310406 A2 | 4/1989 |
| EP | 0414513 A2 | 2/1991 |
| EP | 0456303 A2 | 11/1991 |
| EP | 0505636 | 9/1992 |
| EP | 0284232 | 9/1998 |
| EP | 1045248 A2 | 10/2000 |
| EP | 1901067 A2 | 3/2008 |
| EP | 2031393 A1 | 3/2009 |
| EP | 2072135 A1 | 6/2009 |
| GB | 1244321 A | 8/1971 |
| KR | 20020097364 A | 12/2002 |
| WO | 8204263 A1 | 12/1982 |
| WO | 88/08534 | 11/1988 |
| WO | 91/12366 | 8/1991 |
| WO | 9813519 A1 | 4/1998 |
| WO | 9836821 A1 | 8/1998 |
| WO | 02059299 A2 | 8/2002 |
| WO | 02077013 A2 | 10/2002 |
| WO | 03016902 A1 | 2/2003 |
| WO | 2004/097419 A1 | 11/2004 |
| WO | 2005091878 A2 | 10/2005 |
| WO | 2007/097917 A1 | 8/2007 |
| WO | 2008154237 A2 | 12/2008 |
| WO | 2009034563 A2 | 3/2009 |
| WO | 2011014763 A1 | 2/2011 |

OTHER PUBLICATIONS

Non-Final Office Action dated Nov. 3, 2015 from related U.S. Appl. No. 13/360,528.

Official Action dated Aug. 4, 2014 issued in related U.S. Appl. No. 13/789,002, filed Mar. 7, 2013.

Non-Final Office Action dated Jul. 6, 2015 from related U.S. Appl. No. 13/930,628.

Notice of Allowance dated Mar. 6, 2013, issued in related U.S. Appl. No. 13/445,233.

Harlow et al., Antibodies: A Laboratory Manual, 1988, Cold Spring Harbor Laboratory Press, Cold Spring Harbor.

Fundamental Immunology, 3rd ed. (1993), ed. Paul, Raven Press, New York, N.Y.

(56) References Cited

OTHER PUBLICATIONS

Jonio et al., Immunoglobulin Genes, 2nd Ed., 1995, Academic Press, San Diego.
Notice of Allowance dated Jul. 8, 2011, issued in related U.S. Appl. No. 12/533,721.
Notice of Allowance dated Mar. 22, 2012, issued in related U.S. Appl. No. 13/221,116.
Non-Final Office Action dated Dec. 19, 2012, issued in related U.S. Appl. No. 13/445,233.
Notice of Allowance dated Jan. 12, 2016 in related U.S. Appl. No. 13/930,628.
Notice of Allowance dated Mar. 16, 2016 for U.S. Appl. No. 13/789,002.
Notice of Allowance dated Jun. 10, 2016 in U.S. Appl. No. 13/360,528.

* cited by examiner

Figure 1
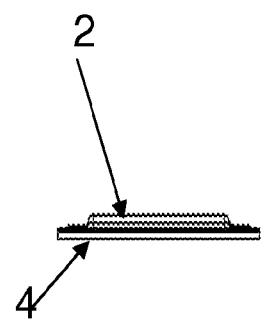
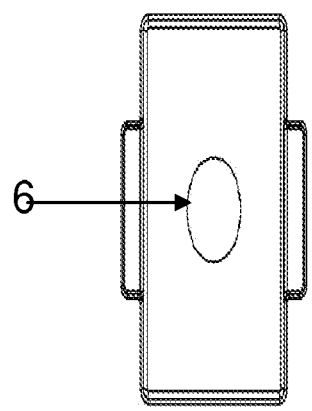

Figure 8
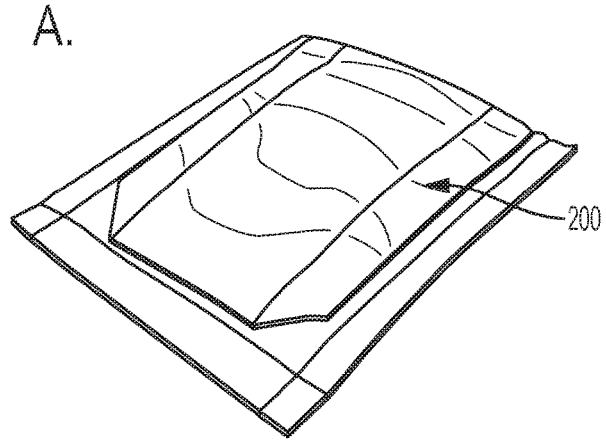
A.
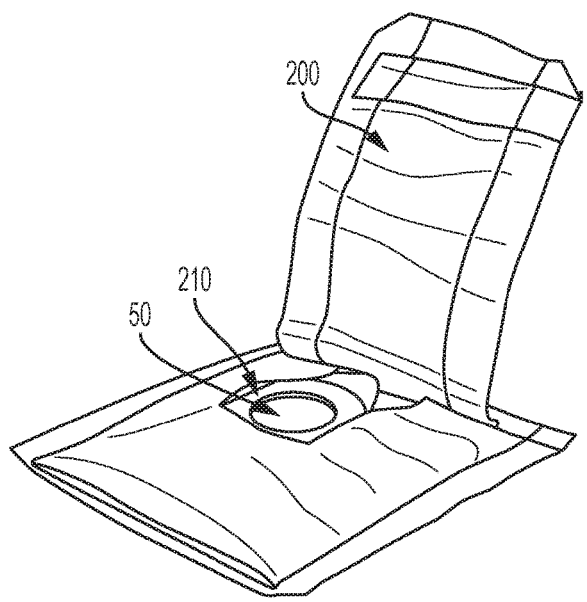
B.
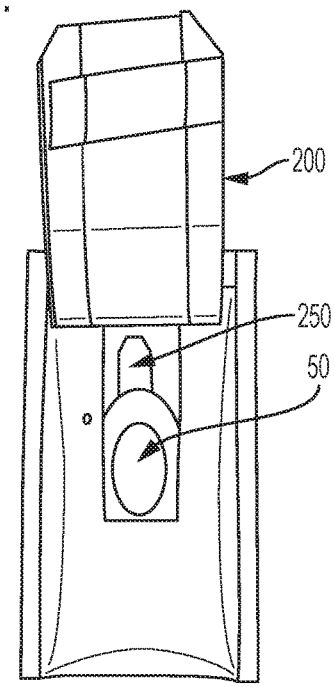
C.

Figure 9
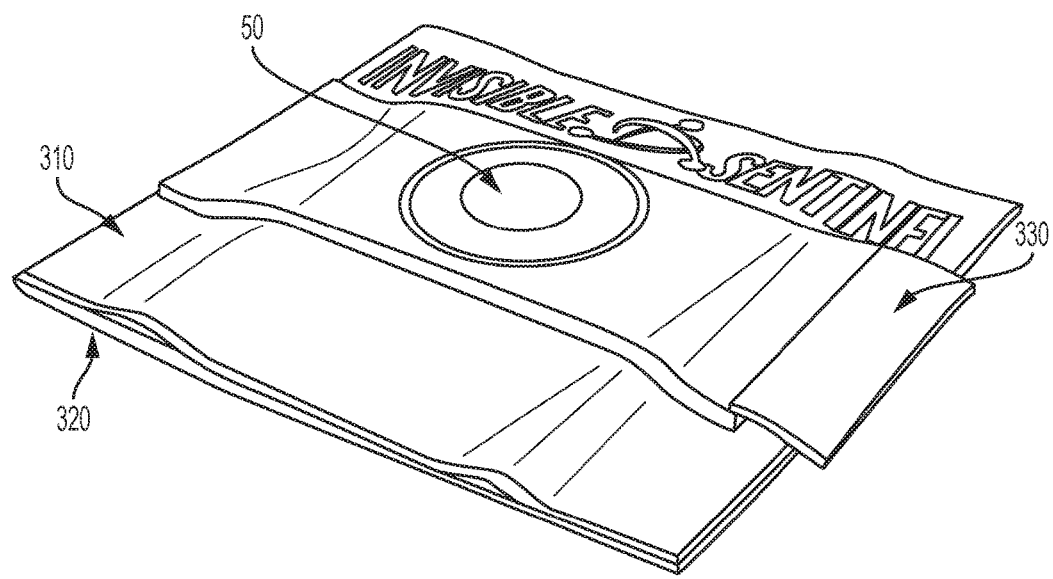
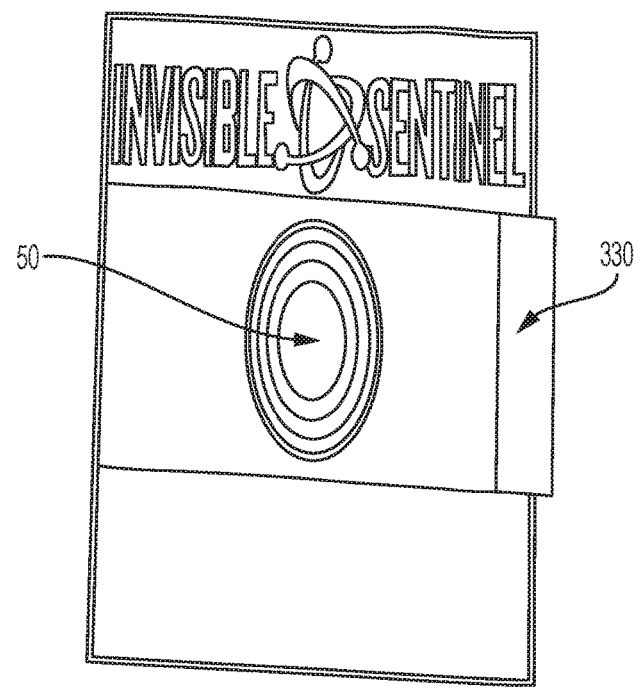

DEVICE FOR DETECTION OF ANALYTES AND USES THEREOF

CROSS REFERENCE TO RELATED APPLICATIONS

The present application claims priority to U.S. Provisional Application No. 61/250,286, filed Oct. 9, 2009, which is hereby incorporated by reference in its entirety.

FIELD OF THE INVENTION

The present invention is directed, in part, to a device and assay for detecting one or more antigens and methods of using the same.

BACKGROUND OF THE INVENTION

Detection of antigens is important for many areas of scientific research, diagnostic use and therapeutic uses. There are several methods by which antigens can be detected. Various methods are described in U.S. Pat. No. 5,160,701, U.S. Pat. No. 5,141,850, PCT Publication WO 91/12336, U.S. Pat. No. 5,451,504, U.S. Pat. No. 5,559,041, European Patent Application No.: 0505636A1, PCT Publication No. WO 88/08534, European Patent Application No. 0284 232A1, U.S. Patent Application Publication No. 20070020768 and U.S. Pat. No. RE39664. The methods and devices available prior to the present invention may still require improvements in sensitivity or speed at which results can be obtained. These factors can be important where time is of the essence when attempting to determine the presence or absence of an antigen.

In the area of detecting food borne pathogenic contaminants, approximately, seventy-six million people in the United States become afflicted with a food borne illness. Of those seventy-six million, approximately, 325,000 will become violently ill, requiring hospitalization, and approximately 5,000 will die. The majority of food-borne illnesses are causes by *Salmonella, E. coli*, and *Campylobacter* costing approximately $35 billion dollars.

Current measures at ensuring a safe food supply involve a combination of local, state and federal authorities as well as an elaborate system of inspectors and surveillance networks. Food manufacturers are held to certain United States Department of Agriculture, United States Food and Drug Administration, and the National Marine Fisheries Service regulations that are enforceable by law. The USDA has created a system of health inspectors that are charged with performing daily meat, produce, and other consumable products inspections made or processed in manufacturing and processing facilities. These inspections involve a detailed statistical analysis to best ensure safety and sterility of food before it reaches the consumer. Moreover, the majority of the meat industry has adopted irradiation techniques to further demonstrate sterility of products. At a lower level, local and municipal health departments work to ensure that local distributors, restaurants, and retailers follow strict guidelines to ensure a safe food supply. However, despite this elaborate network, food-borne infections are still common.

Once an outbreak is strongly suspected, an investigation begins. A search is made for more cases among persons who may have been exposed. The symptoms and time of onset and location of possible cases are determined, and a "case definition" is developed that describes these typical cases. The outbreak is systematically described by time, place, and person. A graph is drawn of the number of people who fell ill on each successive day to show pictorially when it occurred. Calculating the distribution of cases by age and sex shows whom is affected.

Often the causative microbe is not known, so samples of stool or blood must be collected from ill people and sent to the public health laboratory to make a diagnosis. Each collection and sampling can cost upwards of $500 per test and often takes 2-4 days for analysis (CDC "Food-borne Infections").

Prior to the present invention, to identify the food or other source of the outbreak, the investigators first interview a few persons with the most typical cases about exposures they may have had in the few days before they got sick. In this way, certain potential exposures may be excluded while others that are mentioned repeatedly emerge as source possibilities. Combined with other information, such as likely sources for the specific microbe involved, hypotheses are then tested in a formal epidemiologic investigation. The investigators conduct systematic interviews about a list of possible exposures with the ill persons, and with a comparable group of people who are not ill. By comparing how often an exposure is reported by ill people and by well people, investigators can measure the association of the exposure with illness. Using probability statistics, the probability of no association is directly calculated.

As new food-borne problems emerge there is a need for novel devices and methods for detecting food borne pathogens. The present invention provides a device for the detection of antigens, such as antigens from food-borne bacteria, and fulfills the needs of having a device and assay with increased sensitivity and/or speed of detection. The present invention fulfills other needs as well as will be discussed herein.

SUMMARY OF THE INVENTION

In some embodiments, the present invention provides devices for detecting an antigen. In some embodiments, the device comprises a housing comprising a first housing member and a second housing member, wherein the housing further comprises a) an inlet in the first housing member; b) an antigen detection membrane system comprising a conjugate pad, an adhesive member, a test membrane, and an absorbent member; and c) a force member. In some embodiments, at least a portion of each of the conjugate pad, test membrane, and absorbent member are substantially parallel to each other. In some embodiments, the device has a height of less than about 0.15 cm, a width of less than about 2.1 cm, and a depth of less than about 4.7 cm.

In some embodiments, the force member is a stainless clip. In some embodiments, the first housing member is removable. In some embodiments, the first housing member is attached or in contact with the conjugate pad, wherein the movement or removal of the first housing member moves the conjugate pad or removes the conjugate pad from the device. In some embodiments, the devices comprises a conjugate pad that comprises a first antigen-specific antibody.

In some embodiments, the antigen recognized by the first antigen-specific antibody is a food-borne pathogen antigen.

In some embodiments, the present invention provides devices for detecting an antigen comprising a first outer member and a second outer member comprising: a conjugate pad, a first inner member and a second inner member, wherein the first inner member and second inner member are in contact with each other, wherein the first outer member and first inner member comprise an inlet, and wherein between the first and second inner member an antigen detection membrane system comprising in the following order: a test membrane; and an absorbent member; and wherein at least a portion of each of the conjugate pad, test membrane, and absorbent member are substantially parallel to each other, and wherein the antigen detection membrane system is compressed between the first inner member and second inner member, and wherein the conjugate pad is not compressed between said first and second inner members.

In some embodiments, the present invention provides systems comprising a device as described herein and a buffer container or a sample collector.

The present invention also provides methods of detecting an antigen using any of the devices and/or systems described herein.

In some embodiments, the present invention provides a kit comprising a device as described herein and one or more of a positive control, a negative control, an instruction booklet, a buffer container, and a sample collector, or any combination thereof.

BRIEF DESCRIPTION OF DRAWINGS

FIG. 1 depicts a side view and a top view of a representative device according to some embodiments of the present invention.

FIG. 8 depicts a representative device according to some embodiments of the present invention.

FIG. 9 depicts a representative device according to some embodiments of the present invention.

DESCRIPTION OF EMBODIMENTS

Figure 2:
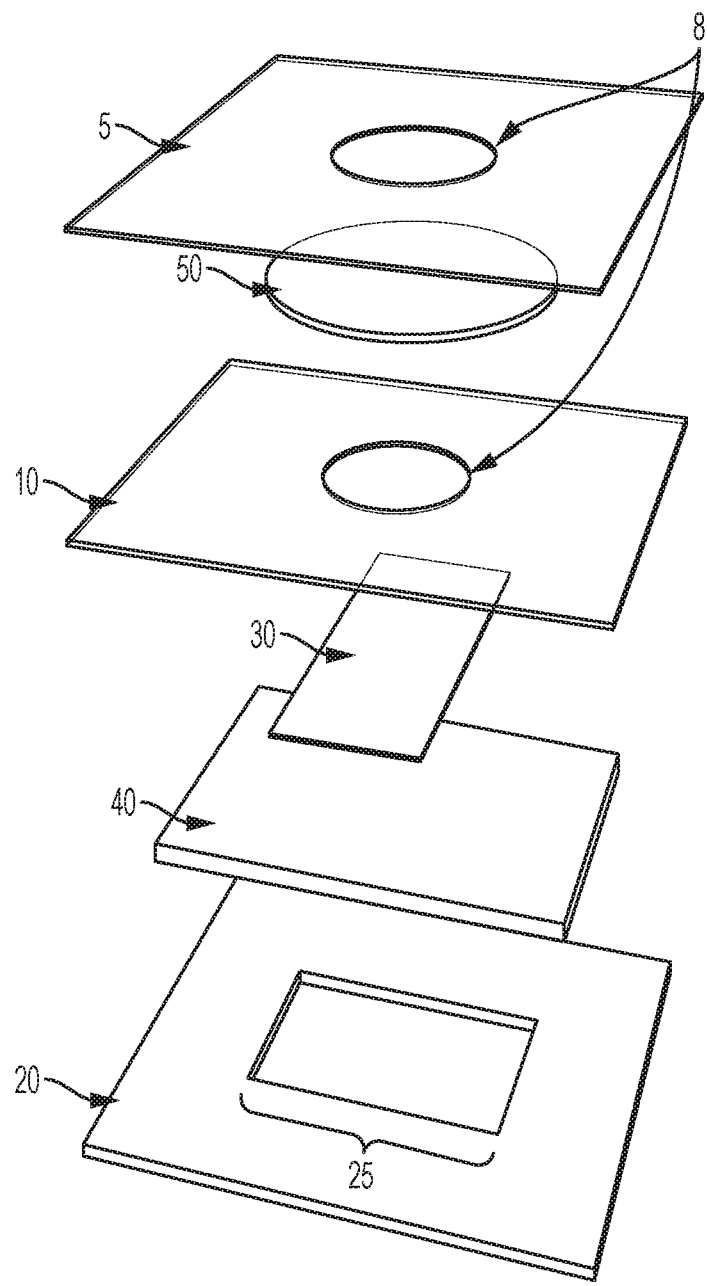
FIG. 2 depicts one type of antigen detection membrane system for a representative device according to some embodiments of the present invention.

As used herein and unless otherwise indicated, the term "about" is intended to mean±5% of the value it modifies. Thus, about 100 means 95 to 105.

The present invention provides devices and methods for detecting antigens or other molecules. In some embodiments, the devices use chromatographic assays. In some embodiments, specific binding assays are employed to indicate the presence or absence of an antigen.

The term "capture reagent" refers to a reagent, for example an antibody or antigen binding protein or a fragment thereof, capable of binding a target molecule or analyte to be detected in a biological sample. A capture reagent may also be, for example, an oligonucleotide or a peptoid.

The term "detecting" or "detection" is used in the broadest sense to include qualitative and/or quantitative measurements of a target analyte.

The terms "attached" or "attachment" can include both direct attachment or indirect attachment. Two components that are directly attached to one another are also in physical contact with each other. Two components that are indirectly attached to one another are attached through an intermediate component. For example, Component A can be indirectly attached to Component B if Component A is directly attached to Component C and Component C is directly attached to Component B. Therefore, in such an example, Component A is indirectly attached to Component B.

The term "isolated" refers to a molecule that is substantially separated from its natural environment. For instance, an isolated protein is one that is substantially separated from the cell or tissue source from which it is derived.

The term "purified" refers to a molecule that is substantially free of other material that associates with the molecule in its natural environment. For instance, a purified protein is substantially free of the cellular material or other proteins from the cell or tissue from which it is derived. The term refers to preparations where the isolated protein is sufficiently pure to be analyzed, or at least 70% to 80% (w/w) pure, at least 80% to 90% (w/w) pure, at least 90 to 95% pure; or at least 95%, at least 96%, at least 97%, at least 98%, at least 99%, or at least 100% (w/w) pure.

The terms "specific binding," "specifically binds," and the like, mean that two or more molecules form a complex that is measurable under physiologic or assay conditions and is selective. An antibody or antigen binding protein or other molecule is said to "specifically bind" to a protein, antigen, or epitope if, under appropriately selected conditions, such binding is not substantially inhibited, while at the same time non-specific binding is inhibited. Specific binding is characterized by a high affinity and is selective for the compound, protein, epitope, or antigen. Nonspecific binding usually has a low affinity. Binding in IgG antibodies for example is generally characterized by an affinity of at least about $10^{-7}$ M, such as at least about $10^{-8}$ M, or at least about $10^{-9}$ M, or at least about $10^{-10}$ M, or at least about $10^{-11}$ M, or at least about $10^{-12}$ M. The term is also applicable where, e.g., an antigen-binding domain is specific for a particular epitope that is not carried by numerous antigens, in which case the antibody or antigen binding protein carrying the antigen-binding domain will generally not bind other antigens. In some embodiments, the capture reagent has a Kd equal to or less than $10^{-9}$M, $10^{-10}$M, or $10^{-11}$M for its binding partner (e.g. antigen). In some embodiments, the capture reagent has a Ka greater than or equal to $10^9 M^{-1}$ for its binding partner.

Capture reagent can also refer to, for example, antibodies. Intact antibodies, also known as immunoglobulins, are typically tetrameric glycosylated proteins composed of two light (L) chains of approximately 25 kDa each, and two heavy (H) chains of approximately 50 kDa each. Two types of light chain, termed lambda and kappa, exist in antibodies. Depending on the amino acid sequence of the constant domain of heavy chains, immunoglobulins are assigned to five major classes: A, D, E, G, and M, and several of these may be further divided into subclasses (isotypes), e.g., IgG1, IgG2, IgG3, IgG4, IgA1, and IgA2. Each light chain is composed of an N-terminal variable domain (VL) and a constant domain (CL). Each heavy chain is composed of an N-terminal variable domain (VH), three or four constant domains (CHs), and a hinge region. The CH domain most proximal to VH is designated CH1. The VH and VL domains consist of four regions of relatively conserved sequences named framework regions (FR1, FR2, FR3, and FR4), which form a scaffold for three regions of hypervariable sequences (complementarity determining regions, CDRs). The CDRs contain most of the residues responsible for specific interactions of the antibody or antigen binding protein with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3. CDR3 is the greatest source of molecular diversity within the antibody or antigen binding protein-binding site. H3, for example, can be as short as two amino acid residues or greater than 26 amino acids. The subunit structures and three-dimensional configurations of different classes of immunoglobulins are well known in the art. For a review of the antibody structure, see Antibodies: A Laboratory Manual, Cold Spring Harbor Laboratory, Eds. Harlow et al., 1988. One of skill in the art will recognize that each subunit structure, e.g., a CH, VH, CL, VL, CDR, and/or FR structure, comprises active fragments. For example, active fragments may consist of the portion of the VH, VL, or CDR subunit that binds the antigen, i.e., the antigen-binding fragment, or the portion of the CH subunit that binds to and/or activates an Fc receptor and/or complement.

Non-limiting examples of binding fragments encompassed within the term "antigen-specific antibody" used herein include: (i) an Fab fragment, a monovalent fragment consisting of the VL, VH, CL and CH1 domains; (ii) an F(ab')$_2$ fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which consists of a VH domain; and (vi) an isolated CDR. Furthermore, although the two domains of the Fv fragment, VL and VH, are coded for by separate genes, they may be recombinantly joined by a synthetic linker, creating a single protein chain in which the VL and VH domains pair to form monovalent molecules (known as single chain Fv (scFv)). The most commonly used linker is a 15-residue (Gly4Ser)$_3$ peptide, but other linkers are also known in the art. Single chain antibodies are also intended to be encompassed within the terms "antibody or antigen binding protein," or "antigen-binding fragment" of an antibody. The antibody can also be a polyclonal antibody, monoclonal antibody, chimeric antibody, antigen-binding fragment, Fc fragment, single chain antibodies, or any derivatives thereof.

These antibodies are obtained using conventional techniques known to those skilled in the art, and the fragments are screened for utility in the same manner as intact antibodies. Antibody diversity is created by multiple germline genes encoding variable domains and a variety of somatic events. The somatic events include recombination of variable gene segments with diversity (D) and joining (J) gene segments to make a complete VH domain, and the recombination of variable and joining gene segments to make a complete VL domain. The recombination process itself is imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation. Based on the estimated number of germline gene segments, the random recombination of these segments, and random VH-VL pairing, up to $1.6 \times 10^7$ different antibodies may be produced (Fundamental Immunology, 3rd ed. (1993), ed. Paul, Raven Press, New York, N.Y.). When other processes that contribute to antibody diversity (such as somatic mutation) are taken into account, it is thought that upwards of $1 \times 10^{10}$ different antibodies may be generated (Immunoglobulin Genes, 2nd ed. (1995), eds. Jonio et al., Academic Press, San Diego, Calif.). Because of the many processes involved in generating antibody diversity, it is unlikely that independently derived monoclonal antibodies with the same antigen specificity will have identical amino acid sequences.

Antibody or antigen binding protein molecules capable of specifically interacting with the antigens, epitopes, or other molecules described herein may be produced by methods well known to those skilled in the art. For example, monoclonal antibodies can be produced by generation of hybridomas in accordance with known methods. Hybridomas formed in this manner can then be screened using standard methods, such as enzyme-linked immunosorbent assay (ELISA) and Biacore analysis, to identify one or more hybridomas that produce an antibody that specifically interacts with a molecule or compound of interest.

As an alternative to preparing monoclonal antibody-secreting hybridomas, a monoclonal antibody to a polypeptide of the present invention may be identified and isolated by screening a recombinant combinatorial immunoglobulin library (e.g., an antibody phage display library) with a polypeptide of the present invention to thereby isolate immunoglobulin library members that bind to the polypeptide. Techniques and commercially available kits for generating and screening phage display libraries are well known to those skilled in the art. Additionally, examples of methods and reagents particularly amenable for use in generating and screening antibody or antigen binding protein display libraries can be found in the literature.

The term "capture reagent" also includes chimeric antibodies, such as humanized antibodies, as well as fully humanized antibodies. In some embodiments the capture reagent is a Goat anti-E. coli 0157:H7 antibody (Cat #: 70-XG13, Fitzgerald Industries); E. coli 0157:H7 mono (Cat #: 10-E13A, Fitzgerald Industries); E. coli 0157:H7 (Cat #: 10C-CR1295M3, Fitzgerald Industries); E. coli 0157:H7 mono (Cat #: 10-E12A, Fitzgerald Industries); or Goat anti-mouse IgG (Cat #: ABSE-020, DCN).

Referring to the drawings, in some embodiments, FIGS. 1 through 9 depict representative devices, components of such representative devices, and various views of such representative devices.

FIG. 1 depicts a representative device comprising a first housing member (2) that further comprises a housing inlet (6), and a second housing member (4). In some embodiments, the first and second housing members can be constructed as a single unit. The housing inlet allows for the introduction of a sample onto the components inside the housing. The housing inlet can be of sufficient size to handle an appropriate amount of volume of a solution that is added to the device. In some embodiments, the size of the opening created by the housing inlet is sufficient to handle about 0.1 to about 3 ml, about 0.1 to about 2.5 ml, about 0.5 to about 2.0 ml, about 0.1 to about 1.0 ml, about 0.5 to about 1.5 ml, about 0.5 to about 1.0 ml, and about 1.0 to about 2.0 ml. In some embodiments, the dimensions of the device are such that any dimension (e.g., width, depth, or height) is less than or equal to about 5.08 cm (2.000 inches). In some embodiments, the height of the device is less than about 0.635 cm (0.250 inches), less than about 0.254 cm (0.100 inches), less than about 0.191 cm (0.075 inches), less than about 0.165 cm (0.065 inches), less than about 0.152 cm (0.06 inches), or less than about 0.140 cm (0.055 inches). In some embodiments, the height of the device is about 0.127 cm (0.050 inches). In some embodiments, the width or depth of the device is less than or equal to about 5.08 cm (2.000 inches), about 4.83 cm (1.900 inches), about 4.699 cm (1.850 inches), about 4.572 cm (1.800 inches), about 4.445 cm (1.750 inches), about 4.191 cm (1.650 inches), about 4.064 cm (1.600 inches), or about 3.81 cm (1.500 inches). In some embodiments, the device is about 0.127 cm (0.050 inches) in height, about 4.445 cm (1.750 inches) in depth, and about 3.81 cm (1.500 inches) in width.

In some embodiments, the device comprises a plurality of components comprising one or more of: a removable member, a conjugate pad, an adhesive member, a test membrane, an absorbent member, a force member, a support member, or any combination thereof.

In some embodiments, the device comprises a force member, a removable member, a conjugate pad, a test membrane, an adhesive member and/or an absorbent member. In some embodiments, the device comprises an antigen detection membrane system. In some embodiments, the antigen detection membrane system comprises a conjugate pad, a test membrane, and an absorbent member. In some embodiments, the antigen detection membrane system comprises an additional permeable membrane, but the device can also be free of a permeable membrane. In some embodiments, the antigen detection membrane system comprises in the following order: a conjugate pad, an adhesive member, a test membrane, and an absorbent member.

FIG. 2 depicts an exploded view of the inside of a representative device comprising a removable member (5), a conjugate pad (50), an adhesive member (10), a test membrane (30), an absorbent member (40), and a support member (20), wherein the support member further comprises an optional support member inlet (25). The removable member and the adhesive member can also comprise optional removable member inlet (8) and adhesive member inlet (12), respectively. Such components could reside within, for example, the device of FIG. 1.

Figure 3:
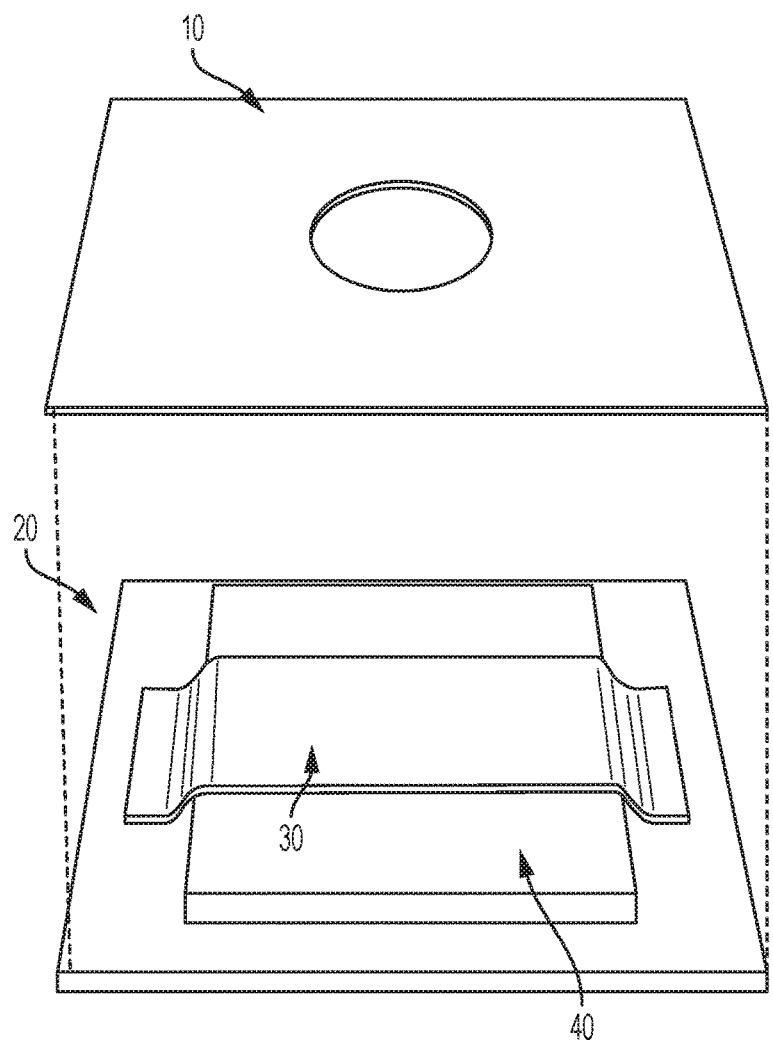
FIG. 3 depicts one type of antigen detection membrane system for a representative device according to some embodiments of the present invention.

FIG. 3 depicts representative components of another representative device comprising an adhesive member (10), a support member (20), a test membrane (30), and an absorbent member (40). As can be seen in FIG. 3, a sample can flow through the adhesive member (10) and contact the test membrane (30).

Figure 4:
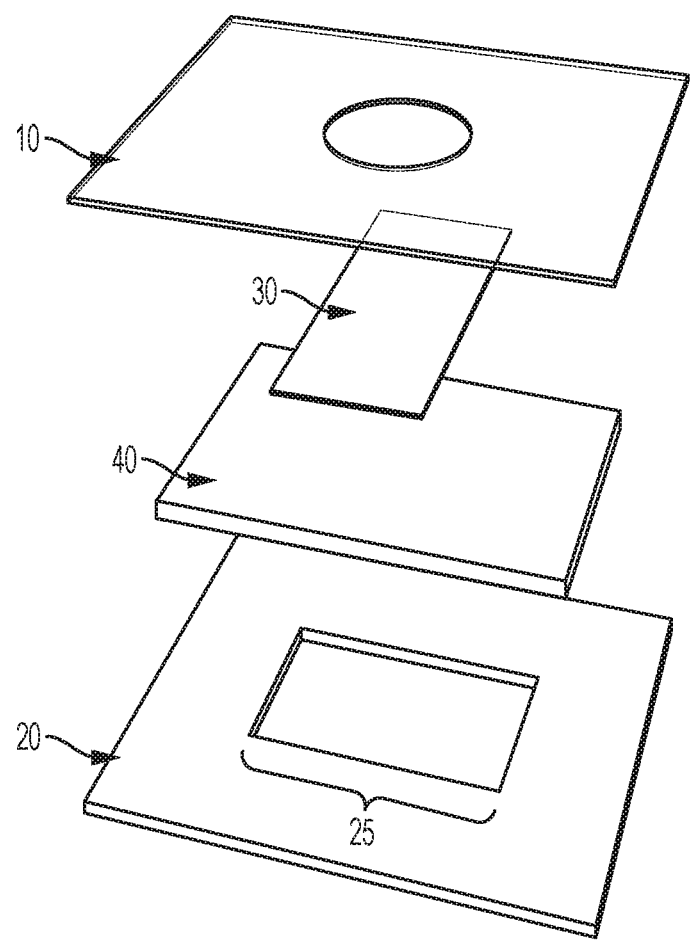
FIG. 4 depicts one type of antigen detection membrane system for a representative device according to some embodiments of the present invention.

FIG. 4 depicts an adhesive member (10), a support member (20), a test membrane (30), and an absorbent member (40). FIG. 4 depicts the components being substantially parallel with one another. FIG. 4 further depicts the support member (20) comprising a support member inlet (25). This inlet can be used to allow the sample to vertically flow through the device.

Figure 5:
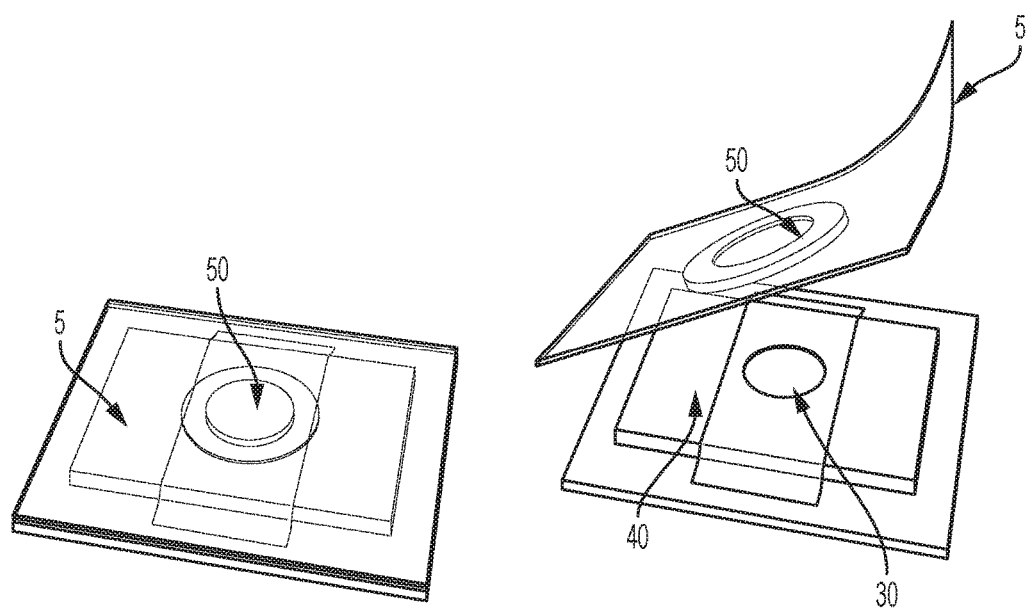
FIG. 5 depicts one type of antigen detection membrane system for a representative device according to some embodiments of the present invention.

FIG. 5 depicts, in part, a conjugate pad (50), a test membrane (30), and an absorbent member (40). FIG. 5 also depicts the conjugate pad in contact and/or attached to a removable member (5). FIG. 5 also depicts the removable member being removed or moved away from the device, which also removes or moves away from the device the conjugate pad. The movement of the conjugate pad allows the test membrane to be visualized, which facilitates analysis and detection of antigens.

Figure 6:
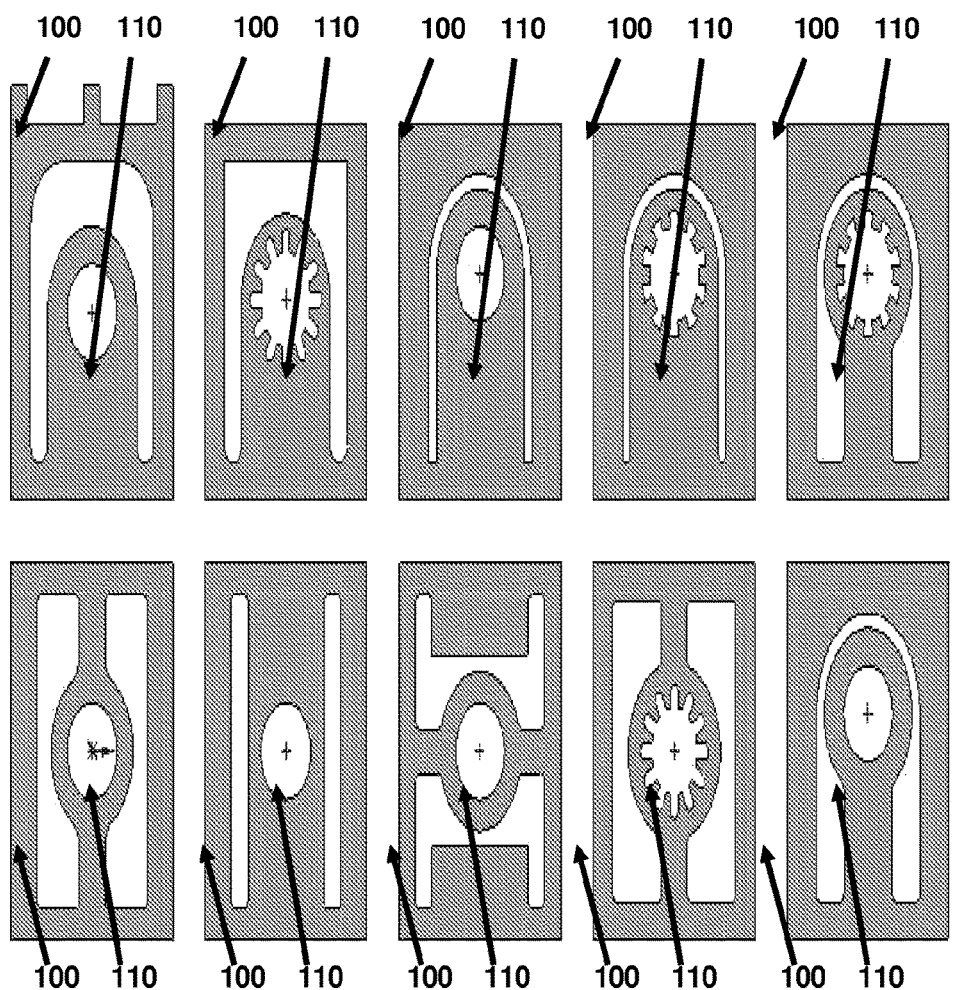
FIG. 6 depicts representative force members for a representative device according to some embodiments of the present invention.
Figure 7:
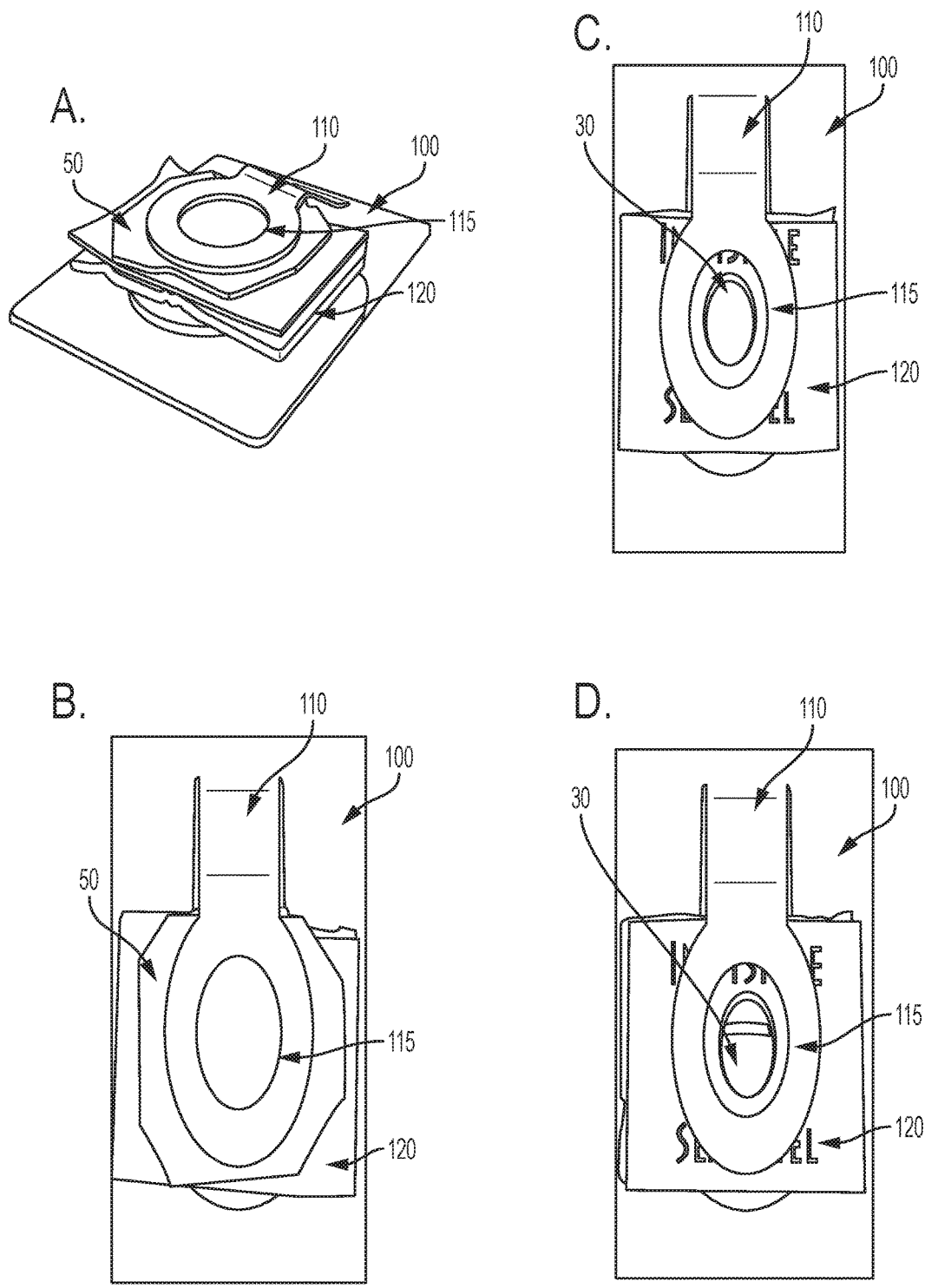
FIG. 7 depicts a representative device according to some embodiments of the present invention.

FIG. 6 depicts examples of force members. Representative force members can come in a variety of shapes, sizes, and configurations, but each member applies pressure on the components that are placed in or on the force member. Each force ember can also comprise an opening (+) into which the analyze sample is applied. FIG. 6 depicts non-limiting examples of force members with a first member (110) and a second member (100).

FIGS. 7A, 7B, 7C, and 7D depict, in part, a force member comprising a first member (110), b) a second member (100), an inlet (115), and an antigen membrane detection system (120). FIGS. 7A and 7B also depict, in part, a conjugate pad (50). The conjugate pad is not seen in FIGS. 7C and 7D. FIGS. 7C and 7D also depict, in part, a test membrane (30) that is part of the antigen membrane detection system. FIG. 7D also depicts in part, a test membrane (30) that has been reacted with a control, which is visualized by the band.

FIG. 8 depicts, in part, a container comprising a removable or movable tab (200), an inlet (210), a conjugate pad (50), and the tab of the conjugate pad (250). The tab of the conjugate pad (255) can be used to remove the conjugate pad (50) from the device to expose the test membrane. For example, a user could pull the tab of the conjugate pad (250) to remove the conjugate pad (50) from the container. What is not visualized is the antigen detection membrane system that is compressed between a first member (110) and a second member (100) as described herein.

FIG. 9, depicts, in part, a first outer member (310), a second outer member (320), a movable or removable tab (330), and a conjugate pad (50). The movable or removable tab (330) comprises an inlet that exposes the conjugate pad (50) so that the sample can be applied to the conjugate pad. FIG. 9 does not show the first inner member (110) and the second inner member (100) compressing the antigen detection membrane system (120). The removable or movable tab (330) when moved or removed, moves or removes the conjugate pad (50), which allows the test membrane to visualized and analyzed.

The removable member inlet within the removable member allows the introduction of a sample onto the conjugate pad. The inlet can be of sufficient size to handle an appropriate amount of volume of a solution that is added to the device. In some embodiments, the size of the inlet is large enough to handle about 0.1 to about 3 ml, about 0.1 to about 2.5 ml, about 0.5 to about 2.0 ml, about 0.1 to about 1.0 ml, about 0.5 to about 1.5 ml, about 0.5 to about 1.0 ml, and about 1.0 to about 2.0 ml. The removable member can also be constructed such that a portion of the removable member is permeable to solutions (i.e., the area defined by the removable member inlet) and another area is impermeable. The permeable area can act as an inlet because it would allow solutions to cross the removable member and contact the conjugate pad. The removable member inlet can have any one of numerous shapes and sizes. In some embodiments, the first housing member serves as the removable member. In other embodiments, the first housing member and the removable member are separate components. In embodiments where the first housing member and the removable member are separate components, at least a portion of the housing inlet and removable member inlet overlap such that a solution can enter through both inlets.

In some embodiments, the removable member contacts a first surface of a conjugate pad. The removable member can also be attached to the conjugate pad. The removable member can be attached to the conjugate pad by any means such that when the removable member is removed from the device or its position is changed, the conjugate pad is also removed or the position of the conjugate pad is also changed. The removable member can be attached to the conjugate pad with, for example, but not limited to, an adhesive. Adhesives include, but are not limited to, glue, tape, or other substance that would allow the removable member and the conjugate pad to be attached to one another.

The removable member, in some embodiments, directly contacts the conjugate pad or indirectly contacts the conjugate pad through another layer. The sample can be, in some embodiments, directly applied to the conjugate pad through the opening in the removable member.

The conjugate pad can be a membrane or other type of material that can comprise a capture reagent. The conjugate pad can be a cellulose acetate, cellulose nitrate, polyamide, polycarbonate, glass fiber, membrane, polyethersulfone, regenerated cellulose (RC), polytetrafluorethylene (PTFE), polyester (e.g., polyethylene terephthalate), polycarbonate (e.g., 4, 4-hydroxy-diphenyl-2, 2'-propane), aluminum oxide, mixed cellulose ester (e.g., mixture of cellulose acetate and cellulose nitrate), nylon (e.g., polyamide, hexamethylenediamine, and Nylon 66), polypropylene, PVDF, high density polyethylene (HDPE)+nucleating agent "aluminum dibenzoate" (DBS) (e.g., 80u 0.024 HDPE DBS (Porex)), and HDPE, or any mixtures thereof. Examples of conjugate pads also include, CYCLOPORE® (polyethylene terephthalate), NUCLEOPORE® (polyethylene terephthalate), MEMBRA-FIL® (cellulose acetate and nitrate), WHATMAN® (cellulose acetate and nitrate), Whatman #12-S (rayon), ANOPORE® (aluminum oxide), ANODISC® (aluminum oxide), Sartorius (cellulose acetate, e.g. 5 μm), and Whatman Standard 17 (bound glass). In some embodiments, the conjugate pad can be a nanoparticle based matrix such as, but not limited to, a 2D sheet or 3D matrix comprised of carbon based nanoparticles, gold or metal alloy nanoparticles, co-polymer matrices, as well as monodisperse semiconducting, magnetic, metallic and ferroelectric nanocrystals.

In some embodiments, the conjugate pad or test membrane, or both, comprises a capture reagent. In some embodiments, the conjugate pad or test membrane, or both, is contacted with the capture reagent and then allowed to dry. The conjugate pad or test membrane, or both, can also comprise other compositions to preserve the capture reagent such that it can be stably stored at room temperature or under refrigeration or freezing temperatures. In some embodiments, the conjugate pad or test membrane, or both, is soaked with a buffer prior to the capture reagent being applied. In some embodiments, the buffer is a blocking buffer that is used to prevent non-specific binding. In some embodiments, the buffer comprises Borate, BSA, PVP40 and/or TWEEN-100 (t-Octylphenoxypolyethoxyethanol), or any mixture thereof. In some embodiments, the buffer is 10 mM Borate, 3% BSA, 1% PVP40, and 0.25% TWEEN-100 (t-Octylphenoxypolyethoxyethanol). In some embodiments the capture reagent is applied to the conjugate pad or test membrane or both in a solution comprising trehalose and sucrose. In some embodiments, the capture reagent is applied to the conjugate pad or test membrane, or both, in a solution comprising trehalose, sucrose and phosphate and/or BSA. In some embodiments, the capture reagent is applied in a solution that is 5% trehalose, 20% sucrose, 10 mM phosphate, and 1% BSA.

In some embodiments, the conjugate pad or test membrane, or both, comprises about 0.5 to about 5.0 μg of a capture reagent, about 1 to about 3 μg of a capture reagent, about 1 to about 2 μg of a capture reagent, about to 2 to about 3 μg of a capture reagent, about 1.5 μg of a capture reagent, about 2.5 μg of a capture reagent, or about 2.7 μg of a capture reagent. In some embodiments, the removable member contacts a first surface of the conjugate pad and the adhesive member contacts a second surface of the conjugate pad.

In some embodiments, the device comprises an adhesive member. The adhesive member can comprises an adhesive member inlet that allows the sample to flow through the conjugate pad and contact the test membrane. In some embodiments, the adhesive member inlet is the same size or shape as the removable member inlet. In some embodiments, the adhesive member inlet is a different size or shape as the removable member inlet. In some embodiments, the inlets in the adhesive member are the same shape but have different areas. Inlets with different areas would be considered to have different sizes. The adhesive member can be made up of any substance suitable for adhering one member or membrane to another member or membrane. In some embodiments, the adhesive member is impermeable to liquid. In some embodiments, the adhesive member contacts the removable member.

The test membrane is a membrane where detection of a binding partner to a capture reagent occurs. Test membranes include, but are not limited to, a nitrocellulose membrane, a nylon membrane, a polyvinylidene fluoride membrane, a polyethersulfone membrane, and the like. The test membrane can be any material that can be used by one of skill in the art to detect the presence of a capture reagent's binding partner (e.g. antigen or epitope). The test membrane can also comprise a capture reagent. In some embodiments, the test membrane is contacted with a capture reagent and the capture reagent is allowed to dry and adhere to the test membrane. Examples of test membranes include, but are not limited to Protran BA83, Whatman, Opitran BA-SA83, and 0.22 μm white plain (Millipore Product No. SA3J036107). Test membranes may also be comprised of nanoparticle matrices to which capture reagents are bound. Nanocrystals can be arranged into 2D sheets and 3D matrices with materials such as, but not limited to, carbon based particles, gold or metal alloy particles, co-polymer matrices, as well as monodisperse semiconducting, magnetic, metallic and ferroelectric nanocrystals. The test membrane can comprise a plurality of capture reagents. In some embodiments, the test membrane comprises 1, 2, 3, 4, 5, 6, 7, 8, 9, or 10 capture reagents. In some embodiments, the test membrane comprises a plurality of areas each with a different capture reagent. In some embodiments, the plurality of areas do not completely overlap or coincide with one another. By using a plurality of capture reagents, multiple binding partners (e.g., epitopes or antigens) can be detected.

In some embodiments, the device also comprises an absorbent member. The absorbent member can also be referred to as a "wicking membrane," a "wick pad" or a "wicking pad." The absorbent member absorbs the fluid that flows through the device when the sample is applied to the device and provides for a wicking force that aids in the flow of the sample when it is applied to the device.

The absorbent member can be any material that can facilitate the flow of the sample through the conjugate pad and to the test membrane. Examples of absorbent members include, but are not limited to cellulose, super absorbent polymers, glass fiber pads (e.g., C083 (Millipore)), and the like. In some embodiments, the device comprises a plurality (e.g., 2 or more) of absorbent members. In some embodiments, the housing comprises 2, 3, 4, or 5 absorbent members. In some embodiments, the device comprises one absorbent member. In some embodiments, the absorbent member comprises one or more membranes up to 10 individual membranes, and each membrane may be the same material or a different material. In some embodiments, the device consists of only 1 membrane that is an absorbent member.

In some embodiments, the device comprises a force member. FIG. 6 depicts representative, but non-limiting examples, of force members. The force member can, in some embodiments, be used to apply pressure or to compress the other components of the antigen detection membrane system against one another. The force member can be made out of any material including, but not limited to stainless steel. The stainless steel can be laser cut such that it can act as a clip. The force member (e.g. clip) acts to apply pressure to the membrane system. The force member is not limited to a clip, but rather can be any shape that can apply pressure to the membrane system (e.g. nanoparticle matrices) and piston like structures strategically placed within the assembly. The force member allows the device to work with vertical flow as opposed to relying upon lateral flow. In some embodiments, the force member contacts a surface of the absorbent member. In some embodiments, the force member contacts a surface of the absorbent member and a surface of the removable layer. In some embodiments, the force member compresses the membrane detection system from above and below the membrane detection system. For example, the force member can sandwich all the layers of the membrane detection system. In some embodiments the force member is attached to the support member. See, for example, FIG. 7C showing a component (110) attached to component (100).

In some embodiments, the device comprises, in the following order, a removable member, a conjugate pad, and an adhesive member.

The device can also comprise a support member. The support member, in some embodiments, contacts a surface of the absorbent member. The support member can also have a support member inlet. The inlet can be the same size and/or shape as the inlet in the removable member and/or the adhesive member. In some embodiments, the support member comprises an inlet that is a different size and/or shape as the inlet in the removable member and/or the adhesive member. The support member can be made from any material including, but not limited to, plastic. In some embodiments, the second housing member serves as the support member.

The devices described herein can be used in assays to detect the presence of a capture reagent's binding partner. For example, an antigen can be detected by an antibody using the devices of the present invention. The devices of the present invention employ vertical flow. "Vertical flow" refers to the direction that the sample flows across the different membranes and members present in the device. Vertical flow refers to a sample flowing through the membrane (e.g., top to bottom) as opposed to lateral flow, which refers to a sample flowing across (e.g., side to side) a membrane, pad or absorbent member. In a lateral flow device, the membranes and pads sit horizontally adjacent to one another substantially on the same plane. In a vertical flow device, each membrane or pad is substantially parallel or completely parallel to each other and occupy substantially different spatial planes in the device. The membranes and pads may occupy similar planes when they are compressed or put under pressure. In some embodiments, at least a portion of each member, membrane or pad is layered on top of each other. In some embodiments, at least a portion of each layer of member, membrane or pad is substantially parallel to each other. In some embodiments, at least a portion of each layer is in a different spatial plane than each other layer.

To allow vertical flow to occur efficiently, in some embodiments, the conjugate pad, the test membrane and the absorbent member are substantially parallel to each other. In some embodiments, the conjugate pad, test membrane, and the absorbent member are present in different spatial planes. In some embodiments, the housing also comprises a hydrophobic membrane (not shown) that can slow or stop the vertical flow of the sample. The hydrophobic membrane can be in contact with the test membrane, which would allow the sample to dwell or rest upon the test membrane. The dwell can allow for increased sensitivity and detection. The vertical flow is modulated by the pressure that is applied to the membrane, pad, and members. In some embodiments, the pressure is applied perpendicular to the test membrane and/or the conjugate pad. The pressure can be applied so that the conjugate pad is compressed against the housing.

The force member can apply pressure that is substantially perpendicular to the test membrane. The pressure facilitates the vertical flow. The pressure allows each component of the antigen detection membrane system to be in contact with another component. The pressure can also be relieved to stop the flow so that the test sample can dwell or rest upon the test membrane, which can allow for greater sensitivity. The pressure can then be reapplied to allow the vertical flow to continue by allowing the sample to flow into the absorbent member(s). The force member can apply pressure such that the conjugate pad contacts a portion of the housing (e.g., first housing member or removable layer). In some embodiments, the conjugate pad contacts the housing when it is not under the pressure being exerted by the force member but upon the force member exerting pressure the conjugate pad is compressed against a portion of the housing.

In some embodiments, the conjugate pad contacts the perimeter of the housing inlet. The housing inlet can also comprise a collar or other similar feature, such as an O-ring. In some embodiments, the conjugate pad contacts the perimeter of a collar and/or an O-ring. In some embodiments, the conjugate pad is capable of being compressed against the perimeter of the housing inlet, which can include, in some embodiments, a collar and/or an O-ring.

"Capable of being compressed against the perimeter of the housing inlet" refers to a membrane or pad (e.g., conjugate pad) being compressed either directly in contact with the perimeter of the housing inlet or being compressed against another layer or material (e.g., membrane) that is in contact with the perimeter of the housing inlet.

In some embodiments, the conjugate pad is not in direct physical contact with the housing but is in fluid contact with the housing. "Fluid Contact" means that if a sample is applied to the device through the housing inlet or other opening, the fluid will contact the conjugate pad. In some embodiments, the conjugate pad can be separated from the housing by another membrane, such as a permeable membrane, where the other membrane is in direct physical contact with the housing or in direct physical contact with the collar or O-ring. When the sample is applied to the device, the fluid can contact the other membrane first and then contact the conjugate pad. This is just one example of the conjugate pad being in fluid contact with the housing. There are numerous other embodiments where the conjugate pad is not in direct physical contact with the housing, the collar, or the O-ring, but is in fluid contact with the housing.

The force member can apply any pressure that is sufficient to facilitate vertical flow across the different layers. In some embodiments, the force is less than 1 lbf. The force can also compress a hydrophobic or impermeable membrane as well if one is present in the device.

In some embodiments, the force member contacts a first surface of an absorbent member. In some embodiments, a conjugate pad contacts a test membrane. In some embodiments, a first surface of a test membrane contacts a permeable membrane. In some embodiments, a second surface of the test membrane contacts a second surface of the absorbent pad. In some embodiments, the device comprises a hydrophobic membrane, and, for example, the hydrophobic membrane contacts a second surface of the test membrane. In some embodiments, the hydrophobic membrane contacts a first surface of the absorbent pad. In some embodiments, a conjugate pad contacts an adhesive member. In some embodiments, a test membrane contacts an adhesive member.

In some embodiments, a first surface of the conjugate pad contacts the housing and a second surface of the conjugate pad contacts a first surface of the adhesive member, wherein the second surface of the adhesive member contacts a first surface of the test membrane, wherein a second surface of the test membrane contacts a first surface of the absorbent pad, wherein a second surface of the absorbent pad contacts the support member. In some embodiments, the first surface of the conjugate pad contacts a perimeter of the housing inlet. In some embodiments, the first surface of the conjugate pad contacts a perimeter of a collar or an O-ring.

In some embodiments, any one or more of the inlets comprise an opening chosen from a range of about 0.2 to about 20 cm$^2$. In some embodiments, any one or more of the inlets is about 1 to about 2 cm in diameter. In some embodiments, any one or more of the inlets is about 1 or about 1.5 cm in diameter. In some embodiments, any one or more of the inlets is about 1, about 2, about 3, about 4, or about 5 cm in diameter.

In some embodiments, a device for detecting an antigen comprises a first member and a second member. In some embodiments, the first member and second member are in contact with each other. In some embodiments, the first member comprises one or more inlets. In some embodiments, between the first and second member is an antigen detection membrane system. In some embodiments, the antigen detection membrane system between the first and second member comprises a conjugate pad, an adhesive member, a test membrane and an absorbent member. In some embodiments, the antigen detection membrane system comprises in the following order: a conjugate pad; an adhesive member; a test membrane; and an absorbent member. As discussed herein, in some embodiments, at least a portion of each of the conjugate pad, test membrane, and absorbent member are substantially parallel to each other.

In some embodiments, the antigen detection membrane system is compressed between the first and second member (e.g. of the force member). In some embodiments, the antigen detection membrane system is compressed between a plane formed by the first member and a plane formed by the second member wherein the planes formed by the first and second members are substantially parallel to each other and the antigen detection membrane system. In some embodiments, the planes are parallel to each other and the antigen detection membrane system. In some embodiments, the first and second members that compress the antigen membrane detection system is a force member. For example, the force member can be referred to as comprising a first and second member to create the force that compresses the antigen membrane detection system.

In some embodiments, the first and second member are attached to one another along an edge of the first member that is parallel to an edge of the second member. In some embodiments, the first and second member are attached by a spring, hinge, and the like. The manner by which the first and second member are attached is not limited and can be by any structure that enables the antigen membrane system to be compressed between the first and second member. In some embodiments, the first and second member are contiguous with one another and form a clip. Examples of clips (e.g. force members) are shown throughout the present application (e.g. FIG. 6). The clip, can be for example cut from metal or other type of material that allows the first member to be flexible such that the antigen membrane detection system can be inserted between the first and second members. In some embodiments, the first member is removable.

In some embodiments, the first member is attached or in contact with the conjugate pad, wherein the movement or removal of the first member moves the conjugate pad or removes the conjugate pad from the device. In some embodiments, the conjugate pad is removable.

In some embodiments, the conjugate pad is removed from the device comprising the first and second member by removing only the conjugate pad.

In some embodiments, the conjugate pad comprises a tab. The tab can be used to remove or to facilitate the removal of the conjugate pad.

In some embodiments, the devices described herein are placed in a container. In some embodiments, the container is a pouch or a bag. In some embodiments, the container comprises an inlet. In some embodiments, the container comprises a removable or movable member or layer that when moved or removed exposes the inlet allowing the sample to be applied to the antigen detection membrane system. Examples of a removable or movable member or layer includes, but is not limited to, a flap or tab. A flap or tab, for example, is shown in FIGS. 8 and 9. In some embodiments, the removable layer or movable layer can also act as a seal for the container. The seal can protect the conjugate pad and/or the antigen membrane detection system.

In some embodiments of the devices and systems described herein, the removable or movable layer is in contact with or attached to the conjugate pad.

In some embodiments, a device for detecting an antigen comprises a first outer member and a second outer member comprising a first inner member and a second inner member, wherein the first inner member and second inner member are in contact with each other. In some embodiments, the first outer member comprises an inlet. In some embodiments, the first inner member comprises an inlet. In some embodiments, the first outer member and the first inner member comprise an inlet. In some embodiments, between the first and second inner members is an antigen detection membrane system. In some embodiments, the device comprises a conjugate pad. In some embodiments, the device lacks a conjugate pad. In some embodiments, the antigen detection membrane system comprises a test membrane and an absorbent member and optionally a conjugate pad. In some embodiments, the antigen detection membrane system comprises in the following order a test membrane and an absorbent member. In some embodiments, at least a portion of each of the optional conjugate pad, test membrane, and absorbent member are substantially parallel to each other. In some embodiments, as discussed above, the antigen detection membrane system is compressed between the first inner member and second inner member. In some embodiments, the device and/or system comprises an adhesive member as described herein. In some embodiments, the device comprises a filtration membrane. In some embodiments, the filtration membrane can be within the antigen detection membrane system. In some embodiments, the a first surface of the filtration membrane contacts a surface of the first inner member and a second surface of the filtration membrane contacts another membrane or member of the antigen detection membrane system. In some embodiments, a second surface of a filtration membrane contacts a surface of a test membrane. The filtration membrane can be any material as described herein. For example, the filtration membrane, in some embodiments, can be the same materials that can be a conjugate pad, test, membrane, absorbent member, and the like. In some embodiments, the filtration membrane is a glass fiber pad.

In some embodiments, where the conjugate pad is not present within the device or the system, the conjugate is supplied as a liquid or as a material that can be dissolved in a liquid (e.g. water, buffered solution, saline, and the like). The conjugate can be supplied in a separate container (e.g. tube) and be provided with a device or system described herein. Where the conjugate is supplied in a container the conjugate is incubated with the sample before the sample is applied to the antigen detection membrane system. The sample can be produced by any method and/or as described herein. For example, a piece of meat can be swabbed or wiped and to produce a test sample. The test sample can then be incubated or contacted with the conjugate to produce a test sample-conjugate mixture. This mixture can then be applied to the antigen detection membrane system as described herein using a device and/or system as described herein. In some embodiments, the test sample-conjugate mixture is applied directly to the test membrane. In some embodiments, the test sample-conjugate mixture is filtered or passes through another membrane prior to contacting the test membrane.

In some embodiments, the antigen detection membrane system is compressed between the first and second inner members. In some embodiments, the antigen detection membrane system is compressed between a plane formed by the first inner member and a plane formed by the second inner member wherein the planes formed by the first inner member and the second inner member are substantially parallel to each other and the antigen detection membrane system. In some embodiments, the planes are parallel to each other and the antigen detection membrane system. In some embodiments, the planes are substantially parallel to the first and second outer members.

In some embodiments of the devices described herein and throughout, the conjugate pad is not compressed by the first and second inner members or by the force members described herein.

In some embodiments, the first outer member comprises a removable or movable tab. In some embodiments, the conjugate pad is attached to said first outer member. In some embodiments, the conjugate pad is attached to the removable or movable tab. In some embodiments, the first outer member and second outer member form a container and the container encapsulates the first and inner second member. In some embodiments, the container is a pouch, bag (e.g. sealable (e.g. zipper, adhesive, and the like) or any other type of container that can encompass the antigen membrane detection system and that is compressed between the first and second inner members.

In some embodiments, the container comprises a removable or movable tab. The removable or movable tab can be any shape and can be completely removable or removed to an extent that exposes the inlet. In some embodiments, the tab when moved or removed removes or moves the conjugate pad. The conjugate pad can be moved, for example, a sufficient distance so that the results of the test membrane can be analyzed (e.g. visualized).

In some embodiments, a first surface of the conjugate pad is in contact with the first outer member and a second surface of the conjugate pad is in contact with the first inner member.

In some embodiments, the first and second inner members are attached to one another along an edge of the first inner member that is parallel to an edge of the second inner member. In some embodiments, the first and second inner members are attached by a spring, hinge, and the like. The manner by which the first and second inner members are attached is not limited and can be by any structure that enables the antigen membrane system to be compressed between the first and second member. In some embodiments, the first and second inner members are contiguous with one another and form, for example, a clip. Examples of clips are shown throughout the present application. The clip, can be for example, cut from metal or other type of material that allows the first inner member to be flexible such that the antigen membrane detection system can be inserted between the first and second members. In some embodiments, the first inner member is removable.

As discussed herein, the devices and systems can comprise a removable or movable layer (e.g. tab). The removable or movable layer can be removed or moved by manual force, such as, but not limited to, peeling or tearing. The removable or movable layer can also be removed or moved by mechanical force. The manner by which the removable or movable layer is moved can by any means. Examples of a removable or movable layer includes but is not limited to, tabs, flaps, and the like. As discussed herein, this flap or tab can act as a seal and the like.

As discussed herein, the conjugate pad can comprise an antigen specific capture reagent. In some embodiments, the conjugate pad comprises a plurality of antigen specific capture reagents. In some embodiments, the conjugate pad comprises 1, 2, 3, 4, or 5 antigen specific capture reagents. The antigen can be any molecule that can be specifically recognized by a capture reagent. Examples of antigens include a polynucleotide molecule (e.g., DNA, RNA, siRNA, antisense oligonucleotide) a peptide, a protein, a saccharide, a polysaccharide, a carbohydrate, and the like. The antigen can also refer to different epitopes present on the same protein or polypeptide.

The capture reagent can also be, for example, protein A, protein G, and the like.

In some embodiments, the detected protein is a pathogen protein. A pathogen protein refers to a protein that is from a pathogen. Examples of pathogens include, but are not limited to, viruses, prokaryote, and eukaryotic organisms such as unicellular pathogenic organisms and multicellular parasites. Pathogens also can include protozoan pathogens which include a stage in the life cycle where they are intracellular pathogens. As used herein, the term "intracellular pathogen" is meant to refer to a virus or pathogenic organism that, at least part of its reproductive or life cycle, exists within a host cell and therein produces or causes to be produced, pathogen proteins.

Bacterial pathogens include, but are not limited to, bacterial pathogenic gram-positive cocci, which include, but are not limited to: pneumococcal, staphylococcal, and streptococcal. Pathogenic gram-negative cocci include, but are not limited to: meningococcal and gonococcal. Pathogenic enteric gram-negative bacilli include, but are not limited to: enterobacteriaceae, *pseudomonas*, acinetobacteria, *eikenella*, melioidosis, *salmonella*, shigellosis, *haemophilus*, chancroid, brucellosis, tularemia, *yersinia* (*pasteurella*), *streptobacillus moniliformis* and *spirillum, listeria monocytogenes, erysipelothrix rhusiopathiae*, diphtheria, cholera, anthrax, donovanosis (granuloma inguinale), and bartonellosis. Pathogenic anaerobic bacteria include, but are not limited to: tetanus, botulism, other clostridia, tuberculosis, leprosy, and other mycobacteria. Pathogenic spirochetal diseases include, but are not limited to: syphilis, treponematoses, yaws, pinta and endemic syphilis, and leptospirosis. Other infections caused by higher pathogen bacteria and pathogenic fungi include, but are not limited to: actinomycosis, nocardiosis, cryptococcosis, blastomycosis, histoplasmosis and coccidioidomycosis, candidiasis, aspergillosis, and mucormycosis, sporotrichosis, paracoccidiodomycosis, petriellidiosis, torulopsosis, mycetoma and chromomycosis, and dermatophytosis. Rickettsial infections include rickettsial and rickettsioses. Examples of mycoplasma and chlamydial infections include, but are not limited to: mycoplasma pneumoniae, lymphogranuloma venereum, psittacosis, and perinatal chlamydial infections. Pathogenic protozoans and helminths include, but are not limited to: amebiasis, malaria, leishmaniasis, trypanosomiasis, toxoplasmosis, *pneumocystis carinii*, babesiosis, giardiasis, trichinosis, filariasis, schistosomiasis, nematodes, trematodes or flukes, and cestode (tapeworm) infections. Bacteria also include *E. coli*, an *Campylobacter*, and a *Salmonella*.

In some embodiments, *E. Coli* is *E. coli* 0157.

Examples of viruses include, but are not limited to, HIV, Hepatitis A, B, and C, FIV, lentiviruses, pestiviruses, West Nile Virus, measles, smallpox, cowpox, ebola, coronavirus, and the like. Other pathogens are also disclosed in U.S. Patent Application Publication No. 2008-0139494, which are incorporated by reference.

In some embodiments, the pathogen is a food borne pathogen. The antigen can be present on a food borne pathogen. Food borne pathogens are pathogens (e.g., viral or bacterial) that cause illness after eating contaminated food. The food itself does not directly cause the illness, but it is rather the consumption of the food borne pathogen that is present on the food that causes the illness. In some embodiments, the food borne pathogen is *E. coli, Campylobacter*, or *Salmonella*. In some embodiments, the antigen is an antigen chosen from a food borne pathogen antigen. For example, the food borne pathogen antigen can be, but is not limited to, chosen from an *E. coli* antigen, a *Campylobacter* antigen, or a *Salmonella* antigen. In some embodiments, the antigen is the species specific O-Antigen. In some embodiments, the O-antigen is the *E. coli* and/or the*Salmonella* O-antigen and can be used for *E. coli* and *Salmonella* detection. In some embodiments, the antigen is a flagellin antigen. In some embodiments, the antigen is the *Campylobacter* flagellin antigen.

In some embodiments, the capture reagent comprises a detection reagent. The detection reagent can be any reagent that can be used to detect the presence of the capture reagent binding to its specific binding partner. The capture reagent can comprise a detection reagent directly or the capture reagent can comprise a particle that comprises the detection reagent. In some embodiments, the capture reagent and/or particle comprises a color, colloidal gold, radioactive tag, fluorescent tag, or a chemiluminescent substrate. In some embodiments, the capture reagent or particle comprises a nanocrystal, up-converting nanoparticles, cadmium selenide/cadmium sulfide fusion nanoparticles, quantum dots, and a Near-Infared (NIR) fluorophore or material (like but not limited to materials such as lanthanide clusters and phthalocyanines, as well as light emitting-diodes consisting of CuPc, PdPc, & PtPc) capable of emitting light in the NIR spectrum. The particle can be, for example, a viral particle, a latex particle, a lipid particle, or a fluorescent particle. In some embodiments, the colloidal gold has a diameter size of: about 20 nm, about 30 nm, or about 40 nm or in the range of about 20 to about 30 nm, about 20 to about 40 nm, about 30 to about 40 nm, or about 35 to about 40 nm. In some embodiments, the particle comprises a metal alloy particle. In some embodiments, the metal alloy particle has a diameter from about 10 to about 200 nm. Examples of metal alloy particles include, but are not limited to, gold metal alloy particles, gold-silver bimetallic particles, silver metal alloy particles, copper alloy particles, Cadmium-Selenium particles, palladium alloy particles, platinum alloy particles, and lead nanoparticles.

In some embodiments, the test membrane also comprises one or more capture reagents.

The capture reagents of the present invention can also include an anti-antibody, i.e., an antibody that recognizes another antibody but is not specific to an antigen, such as, but not limited to, anti-IgG, anti-IgM, or ant-IgE antibody. Where the test membrane comprises an anti-antibody, such as anti-IgG, anti-IgM, or anti-IgE antibody, this non-specific antibody can be used as a positive control to detect whether the conjugate has been released from the conjugate pad. When the sample is applied to the device it allows a first capture reagent to be released from the conjugate pad. As the capture reagent is released and flows through the device, either attached to the antigen or not, it can contact the anti-antibody, such as anti-IgG or anti-IgM antibody, which can then be detected. This detection can be used to show that the device is working properly.

In some embodiments, the test membrane comprises a second antigen specific capture reagent. In some embodiments, the test membrane comprises a first area comprising a first capture reagent comprising an anti-IgG capture reagent; and a second area comprising a second antigen specific capture reagent, wherein the first and second areas do not completely overlap or coincide with one another. This non-limiting embodiment can be used to demonstrate the device is working properly and be used to detect the presence of the antigen of interest.

In some embodiments, the conjugate pad comprises a first antigen specific capture reagent and the test membrane comprises a second antigen specific capture reagent, wherein the first and second antigen specific capture reagents bind to non-competitive epitopes present on the antigen. The device can, for example, employ a sandwich type assay that occurs in two steps. The first step is the binding of the antigen to the capture reagent present in the conjugate pad. After binding to the first antigen specific capture reagent the antigen can flow through to or make contact with the test membrane where a second antigen specific capture reagent is present. Upon interaction with the test membrane if the test antigen can bind to the second antigen-specific capture reagent it will be able to be detected either through visualization or through the use of another detection device such as, but not limited to, a fluorescent reader. The test membrane and the conjugate pad can comprise additional antigen-specific capture reagents that recognize different antigens or different epitopes. In some embodiments, the test membrane or the conjugate pad comprises 1, 2, 3, 4, 5, 6, 7, 8, 9, 10 antigen-specific capture reagents. In some embodiments, the test membrane or the conjugate pad comprises a plurality of antigen-specific capture reagents. In some embodiments, each antigen-specific capture reagent recognizes a different antigen or a different epitope on the same antigen.

"Different antigens" can also refer to the same protein but a protein that is from different strains of the same organism. Different antigens can also refer to antigens from different organisms. For example, there are any many strains of *E. coli*. Not all strains of *E. coli* cause a food-borne illness. The present invention can be used, for example, to detect an antigen from a pathogenic *E. coli* strain as opposed to detecting an antigen from a non-pathogenic *E. coli* strain. In some embodiments, the conjugate pad and/or test membrane comprises a first and a second antigen-specific capture reagents, wherein the first and said second capture reagents recognize different antigens. In some embodiments, the test membrane and/or conjugate pad comprises a plurality of areas comprising a plurality of antigen-specific capture reagents, wherein the plurality of antigen-specific capture reagents recognize different antigens. In some embodiments, the plurality of areas do not completely overlap or coincide with one another. In some embodiments, the plurality of antigens are each independently chosen from an *E. coli* antigen, an *Campylobacter* antigen, and a *Salmonella* antigen. In some embodiments of the present invention, the plurality of antigens is 2, 3, 4, 5, 6, 7, 8, 9, 10, or more than 10 antigens.

The devices may be housed singly, in pairs, or in multiple configurations. The housing can be watertight to prevent leakage and can be manufactured from a variety of inert materials, such as polymer materials. The inlet(s), in some embodiments, can be of sufficient size to contain any required amount of sample or reagents to be used with the invention.

Because the membranes, members, or pads of the device are suitably chemically inert, they may have to be activated at any reaction site where it is desired to immobilize a specific binding reagent against solvent transport. Various methods may be required to render the reagent immobilized according to the particular chemical nature of the reagent. Generally, when the media is nitrocellulose or a mixed nitrocellulose ester, no special chemical linkage is required for the immobilization of reagents. Various techniques may be used for other materials and reagents which include functionalization with materials such as carbonyldiimidazole, glutaraldehyde or succinic acid, or treatment with materials such as cyanogen bromide. Other suitable reactions include treatment with Schiff bases and borohydride for reduction of aldehyde, carbonyl and amino groups. DNA, RNA and certain antigens may be immobilized against solvent transport by baking onto the chromatographic material. Baking may be carried out at temperatures ranging from about 60° C. to about 120° C. for times varying from about five minutes to about 12 hours, and in some embodiments, at about 80° C. for about two hours.

The present invention also provides systems comprising the devices described herein and a buffer container. The buffer container can be any buffer that the sample that is being tested can be mixed with and then applied to the device. For example, the sample can be taken from a source and the sample can be mixed with the buffer. The buffer can be a lysis buffer that will lyse the cells or a buffer that maintains the pH of the sample so that the analysis can be done properly. The buffer container can be any shape and can be included outside or inside the housing of the device.

In some embodiments, the present invention provides a system that comprises a sample collector. The sample collector can be any material that can take a sample from a source and allow the sample to be tested. For example, the sample collector can be a swab, such as a cotton-swab. In some embodiments, the sample collector is an innoculator. In some embodiments, the housing comprises the sample collector and a portion of the sample collector is in the inside of the housing. In some embodiments, the sample collector is partially outside and partially inside the housing. In some embodiments, the sample collector is completely outside the housing.

The present invention also provides for kits comprising the devices described herein. The kit can include a device as described herein, a sample collector, a buffer container, an instruction manual, a positive control, a negative control, or any combination thereof. With respect to the kit, a positive control is a sample that is known to contain the antigen that can be detected with the device present in the kit. In contrast the negative control, would not contain an antigen that can be detected by the kit. The negative control when used in conjunction with the anti-antibody would be able to demonstrate that the device is working properly.

Buffers can also be included in the present invention. Examples of buffers include, but are not limited to, 1×PBS (10 mM phosphate, 137 mM sodium chloride, 2.7 mM potassium chloride), a wash buffer (e.g. 10 mM sodium phosphate, 150 mM NaCl, 0.5% TWEEN-20 (polyoxyethylenesorbitan monolaurate), 0.05% sodium azide, a membrane buffer (e.g. 10 mM sodium phosphate, 0.1% sucrose, 0.1% BSA, 0.2% PVP-40 pH 7.21, filtered with 0.2 µm filter), Polyclonal Conjugate Block Buffer (e.g. 50 mM borate, 10% BSA, pH 8.93); Polyclonal Conjugate Diluent (e.g., 50 mM borate, 1% BSA, pH 9.09), or Blocking Buffers (e.g. 10 mM sodium phosphate, 0.1% sucrose, 0.025% Silwet pH 7.42; 10 mM sodium phosphate, 1% sucrose, 1% trehalose, 0.01% BSA, 0.025% TWEEN-20 (polyoxyethylenesorbitan monolaurate); 0.05% sodium azide, 0.025% Silwet pH 7.4; 10 mM sodium phosphate, 0.1% sucrose, 0.1% BSA, 0.2% PVP-40 pH 7.21). The buffer can also be, but is not limited to, a blocking buffer (e.g. 10% BSA in deionized water, pH 7.4 or 1% BSA in deionized water, pH 7.4); 10 mM Borate, 3% BSA, 1% PVP40, and 0.25% TWEEN-100 (t-Octylphenoxypolyethoxyethanol); and the like.

The conjugate pad and the test membrane can be contacted with any of the buffers described herein either in the presence or absence of a capture reagent and, in some embodiments, allowed to dry.

Examples of buffers that are lysis buffers include, for example, but are not limited to, 2% TWEEN (detergent) (v/v) and 0.1% TRITON (detergent) (v/v); 2% TWEEN (detergent) (v/v) and 0.1% SDS (w/v); 2% TWEEN (detergent) (v/v) and 0.1% BSA (w/v); 2% TWEEN (detergent) (v/v) and 1% BSA (w/v), 0.1% SDS (w/v), 1% BSA (w/v), or any combination thereof. The lysis buffers can also be, for example, 5% TWEEN (detergent)/PBS; 2% TWEEN (detergent)/PBS+0.1% SDS; 2% TWEEN (detergent)/PBS+1% BSA. Other examples of lysis buffers include, but are not limited to, 5% TWEEN-80 (polyoxyethylenesorbitan monooleate) (v/v); 5% Triton X-100 (v/v); 5% NP40 (v/v); 2% TWEEN-80 (polyoxyethylenesorbitan monooleate) (v/v); 2% Triton X-100 (v/v); 2% NP40 (v/v); 1% TWEEN-80 (polyoxyethylenesorbitan monooleate) (v/v); 1% TRITON X-100 t-Octylphenoxypolyethoxyethanol (v/v); and 1% NP40 (v/v). The detergents and other components of the buffers can be made with any suitable buffer suitable for proteins, and includes, but is not limited to, water and phosphate buffered saline. The lysis buffers can be used to prepare the samples prior to the samples making contact with the devices described herein. In some embodiments, a lysis buffer is not used. A lysis buffer is not used on a sample when a surface protein or surface antigen is desired to be detected. Accordingly, in some embodiments, the sample is not subject to lysis or conditions that would cause a cell to be lysed.

The present invention also provides for methods of detecting an antigen comprising contacting a sample using a device and/or system as described herein, wherein the sample contacts the conjugate pad and the test membrane, wherein a positive reaction with the test membrane indicates the presence of the antigen, wherein the conjugate pad comprises a first antigen-specific capture reagent and the test membrane comprises a second antigen-specific capture reagent. A positive reaction is indicated by the capture reagent present in the test membrane binding to an antigen in the test sample. The capture reagent in the test membrane is applied to the test membrane so that it will indicate a positive reaction when it binds to its specific antigen. The specific capture reagent can be applied in any manner such that when it is detected it can form a line, a circle, a plus sign, a broken line, an "X" or any other pattern. In some embodiments, the control line indicating that the device is working properly will cross the antigen specific line and when the antigen specific capture reagent binds to the antigen the detectable label will form a plus sign. The detection can be determined by the detection of the detection reagent as described herein and by routine methods known to one of skill in the art.

In some embodiments, a sample contacts the device, which is then followed by a buffer being applied to the device after the sample has contacted the device. For example, a sample comprising an antigen can be contacted with the conjugate pad such that the sample is transferred to the conjugate pad. Following the contact with the conjugate pad a separate solution can be applied to the device to facilitate or initiate the vertical flow through the devices described herein.

In some embodiments as described herein the capture reagent is an antibody. In some embodiments, the sample that is tested is a solution but can also be a mixture of solution or buffer and solid material that can be applied to the device. The solution will then solubilize the antigen and allow the conjugate pad's capture reagent to come into contact with the antigens present in the sample. In some embodiments, the sample comprises a cell lysate. In some embodiments, the cell lysate has been clarified by centrifugation or other means to remove non-soluble materials.

In some embodiments, the methods comprise contacting a test sample with a sample collector and contacting the sample collector with the device. In some embodiments, the methods comprise contacting the sample collector with a solution or buffer, wherein the solution or buffer is applied to the device. In some embodiments, the samples are contacted with the conjugate pad prior to the sample coming into contact with the test membrane. In some embodiments, the sample is contacted with the conjugate pad and the test membrane simultaneously.

In some embodiments, the methods comprises moving the conjugate pad of the devices described herein, wherein the movement or removal of the conjugate pad exposes the test membrane for detection. In some embodiments, movement or removal of the removable member moves or removes the conjugate pad. In some embodiments, the conjugate pad is attached to the removable member and/or the adhesive member. In some embodiments, when the removable member is moved or removed the adhesive member is also moved with respect to its original position or removed from the device. The antigen that the method can be used to detect can be any antigen. The antigen can be those that are discussed herein or any other antigen that can be detected using the methods and devices described herein. In some embodiments, the method comprises applying the sample to the device and allowing the sample to flow through the device via vertical flow.

The examples provided herein are for the purpose of illustration only and the invention should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A device for detecting an analyte comprising:
a housing comprising a first housing member and a second housing member, wherein the housing comprises:
a) an inlet in the first housing member;
b) an analyte detection membrane system comprising in the following order:
a conjugate pad;
an adhesive member comprising an inlet in fluid contact with the inlet in the first housing member;
a test membrane; and
an absorbent member; and
c) a force member;
wherein at least a portion of each of the conjugate pad, test membrane, and absorbent member are substantially parallel to each other;
wherein the inlet is in fluid contact with the analyte detection membrane system;
wherein the force member is configured to compress the analyte detection membrane system;
wherein the device has a height of less than or about 0.15 cm, a width of less than or about 2.1 cm, and a depth of less than or about 4.7 cm.

2. The device of claim 1, wherein the force member is a clip.

3. The device of claim 1 wherein the first housing member is attached or in contact with the conjugate pad, wherein the movement or removal of the first housing member moves the conjugate pad or removes the conjugate pad from the device.

4. The device of claim 1 wherein the conjugate pad comprises a first analyte-specific capture reagent.

5. The device of claim 4 wherein the analyte recognized by the first analyte-specific capture reagent is a polynucleotide, a peptide, a protein, a saccharide, or a carbohydrate.

6. The device of claim 4 wherein the analyte recognized by the first analyte-specific capture reagent is a pathogen analyte.

7. The device of claim 4 wherein the first analyte-specific capture reagent is a polyclonal antibody, a monoclonal antibody, a chimeric antibody, an Fc fragment, or a single chain antibody.

8. The device of claim 4 wherein the analyte recognized by the first analyte-specific capture reagent is a food-borne pathogen analyte.

9. The device of claim 8 wherein the food-borne pathogen analyte is an analyte from an *E. coli*, a *Campylobacter* species, or a *Salmonella* species.

10. The device of claim 4 wherein the first analyte-specific capture reagent is conjugated to a nanocrystal, up-converting nanoparticles, near-infared (NIR) fluorophore, colloidal gold, fluorescent molecule, radioactive tag, or a chemiluminescent substrate.

11. The device of claim 4 wherein the test membrane comprises a second analyte-specific capture reagent, wherein the second analyte-specific capture reagent and the first analyte-specific capture reagent bind to non-competitive binding sites on the same analyte.

12. The device of claim 11 wherein the test membrane comprises:
 a first area comprising an anti-first analyte-specific antibody; and
 a second area comprising the second analyte-specific antibody;
 wherein the first and second areas do not completely overlap.

13. The device of claim 11 wherein the conjugate pad further comprises a third analyte-specific antibody, wherein the first analyte-specific antibody and the third analyte-specific antibody recognize different analyte.

14. The device of claim 13 wherein the test membrane further comprises a fourth analyte-specific antibody, wherein the fourth analyte-specific antibody and the third analyte-specific antibody bind to non-competitive epitopes on the same analyte.

15. The device of claim 14 wherein the analyte recognized by the first analyte-specific antibody and third analyte-specific antibody are each independently chosen from an *E. coli* analyte, a *Campylobacter* analyte, and a *Salmonella* analyte.

16. A kit comprising the device of claim 1 and one or more of a positive control, a negative control, an instruction booklet, a buffer container, and a sample collector, or any combination thereof.

17. A method of detecting an analyte comprising:
 contacting a sample with the conjugate pad of the device of claim 1;
 moving the conjugate pad to expose the test membrane; and
 identifying a positive or negative reaction for the analyte;
 wherein the sample vertically flows from the conjugate pad to the test membrane.

18. The method of claim 17, wherein the conjugate pad is moved by removing or moving a portion of the first housing member that is operatively connected to the conjugate pad.

19. A device for detecting an analyte comprising:
 a first member and a second member in contact with each other
 wherein said first member comprises an inlet, and
 wherein between the first and second member is an analyte detection membrane system comprising in the following order:
  a conjugate pad;
  an adhesive member comprising an inlet in fluid contact with the inlet in the first housing member;
  a test membrane; and
  an absorbent member; and
 wherein at least a portion of each of the conjugate pad, test membrane, and absorbent member are substantially parallel to each other, and
 wherein said analyte detection membrane system is in fluid contact with inlet and said analyte detection membrane system is compressed between the first and second member.

20. The device of claim 19, wherein said first and second member are attached to each other with a hinge or spring or wherein the first and second member are contiguous and form a clip.

21. The device of claim 19 wherein the first member is attached or in contact with the conjugate pad, wherein the movement or removal of the first member moves the conjugate pad or removes the conjugate pad from the device.

22. The device of claim 19, wherein said conjugate pad is removable.

23. The device of claim 19, wherein said conjugate pad further comprises a tab.

24. The device of claim 23, wherein said tab is configured to remove the conjugate pad when the tab is moved.

25. The device of claim 19, wherein said first and second member are attached to one another along an edge of the first member that is parallel to an edge of the second member.

26. A method of detecting an analyte comprising:
 contacting a sample with the conjugate pad of the device of claim 19;
 moving the conjugate pad to expose the test membrane; and
 identifying a positive or negative reaction for the analyte;
 wherein the sample vertically flows from the conjugate pad to the test membrane.

\* \* \* \* \*